United States Patent [19]

Uhmann et al.

[11] Patent Number: 4,691,008

[45] Date of Patent: Sep. 1, 1987

[54] PROCESS FOR THE LOW-RACEMIZATION PREPARATION OF PEPTIDE INTERMEDIATES OF THE SYNTHESIS OF GONADORELIN AND GONADORELIN ANALOGS, AND NEW INTERMEDIATES FOR THIS PROCESS

[75] Inventors: Rainer Uhmann, Kriftel; Kurt Radscheit, Kelkheim, both of Fed. Rep. of Germany

[73] Assignee: Hoechst Aktiengesellschaft, Fed. Rep. of Germany

[21] Appl. No.: 715,418

[22] Filed: Mar. 25, 1985

[30] Foreign Application Priority Data

Mar. 27, 1984 [DE] Fed. Rep. of Germany ......... 341124

[51] Int. Cl.$^4$ .......................... C07K 1/02; C07K 5/08; C07K 7/06
[52] U.S. Cl. .................................. 530/339; 530/331; 530/330
[58] Field of Search .............. 260/112.5 LH; 530/313, 530/339, 331, 330

[56] References Cited

U.S. PATENT DOCUMENTS

| | | | |
|---|---|---|---|
| 3,953,416 | 4/1976 | Folkers et al. | 260/112.5 LH |
| 4,008,209 | 2/1977 | Fujino et al. | 260/112.5 LH |
| 4,024,248 | 5/1977 | Konig et al. | 260/112.5 LH |
| 4,100,274 | 7/1978 | Dutta et al. | 260/112.5 LH |
| 4,481,190 | 11/1984 | Nestor et al. | 260/112.5 LH |
| 4,490,291 | 12/1984 | Fujino | 260/112.5 LH |

OTHER PUBLICATIONS

Biochem. and Biophys. Res. Commun. 45, (1971) 767–773.

Helvetica Chimica Acta 44, 1961, 1991–2002.

*Primary Examiner*—Delbert R. Phillips

[57] ABSTRACT

The invention relates to a process for the preparation of peptides of the formula I $$U-A^1-A^2{}^{13} A^3-A^4-A^5-X \qquad (I)$$

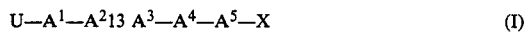

in which
U denotes a urethane protective group,
$A^1$ denotes Trp or D-Trp,
$A^2$ denotes Ser, Ala or Thr,
$A^3$ denotes Tyr or Phe,
$A^4$ denotes Gly, the residue of a D-amino acid or the residue of a D-amino acid derivative,
$A^5$ denotes Leu, N-methyl-Leu, N-ethyl-Leu, Ser(Bu$^t$), Cys(Bu$^t$), Asp(OBu$^t$), Glu(OBu$^t$), Orn(Boc) or Lys(-Boc) and
X denotes OBu$^t$ or $A^6$—Pro—Y,
where
$A^6$ represents Arg, Orn, Lys or homoarginine, and
Y represents Gly—NH$_2$, NH—NH—CO—NH$_2$, (C$_1$–C$_3$)-alkylamino, cyclopropylamino, (C$_1$–C$_3$)-alkylamino which is substituted with hydroxyl or fluorine, or cycloalkylamino which is substituted with hydroxyl or fluorine, using tripeptides of the formula II, $$U-A^1-A^2-A^3-OH,$$

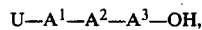

in which the residues are defined as above. The invention also relates to peptides of the formula II as intermediates in this process.

10 Claims, No Drawings

PROCESS FOR THE LOW-RACEMIZATION PREPARATION OF PEPTIDE INTERMEDIATES OF THE SYNTHESIS OF GONADORELIN AND GONADORELIN ANALOGS, AND NEW INTERMEDIATES FOR THIS PROCESS

The invention relates to a process for the preparation of peptides of the formula I $$U-A^1-A^2-A^3-A^4-A^5-X \qquad (I)$$

in which
U denotes a urethane protective group,
$A^1$ denotes Trp or D-Trp,
$A^2$ denotes Ser, Ala or Thr,
$A^3$ denotes Tyr or Phe,
$A^4$ denotes Gly, the residue of a D-amino acid or the residue of a D-amino acid derivative,
$A^5$ denotes Leu, N-methyl-Leu, N-ethyl-Leu, Ser(Bu$^t$), Cys(Bu$^t$), Asp(OBu$^t$), Glu(OBu$^t$), Orn(Boc) or Lys(-Boc) and
X denotes OBu$^t$ or $A^6$—Pro—Y,
where
$A^6$ represents Arg, Orn, Lys or homoarginine, and
Y represents Gly—NH$_2$, NH—NH—CO—NH$_2$, (C$_1$-C$_3$)-alkylamino, cyclopropylamino, (C$_1$-C$_3$)-alkylamino which is substituted with hydroxyl or fluorine, or cycloalkylamino which is substituted with hydroxyl or fluorine, which process comprises reacting a tripeptide of the formula II $$U-A^1-A^2-A^3-OH \qquad (II)$$

in which U, $A^1$, $A^2$ and $A^3$ have the abovementioned meaning, with a peptide of the formula III $$H-A^4-A^5-X \qquad (III)$$

in which $A^4$, $A^5$ and X have the abovementioned meaning, or its derivative.

Peptides of the general formula I are in turn intermediates in the synthesis of gonadorelin (Biochem. Biophys. Res. Commun. 43 (1971) 1334–39) or its analogs, as are disclosed in, for example, U.S. Pat. No. 4,024,248.

As is known, gondadorelin (LHRH) is a hormone from the hypothalamus, which has the formula IV $$\text{Pyr-His-Trp-Ser-Ty-Gly-Leu-Arg-Pro-Gly-NH}_2 \qquad (IV)$$

and which releases the gonadotrophic hormones LH and FSH in the pituitary. Peptides which are suitable as gonadorelin (LHRH) analogs are those in which a few or several of the amino acids in LHRH have been replaced and/or the peptide chain has been modified by shortening, lengthening and/or derivatization. Of particular importance in this context are replacements of glycine in position 6 by D-amino acids and in position 10 by groups such as alkylamino. An example which may be mentioned is buserelin (formula V):

$$\text{Pyr-His-Trp-Ser-Tyr-D-Ser(Bu}^t\text{)-Leu-Arg-Pro-NHEt} \qquad (V).$$

Processes for the preparation of compounds of the formula I are known from the literature (Biochem. Biophys. Res. Commun. 45 (1971) 767; U.S. Pat. No. 4,024,248), in which the synthesis always takes place by the azide method which is known to be a low-racemization process for fragment syntheses of this type (Lit.: J. Chem. Soc. (London) 1960, 3902; Helv. Chim. Acta, 44 (1961) 1991).

Nevertheless, numerous side reactions must be expected when the azide synthesis is used. Thus, it is possible for 1,2-diacylhydrazines to be produced, particularly when an acid deficit prevails during the azide formation.

It is possible for nitration in the o-position to the phenolic hydroxyl group in tyrosine to take place in the present case, and N-nitrosation can take place in tryptophan. The conversion of peptide azides into the corresponding amides has also been observed (summarizing Lit.: Liebigs Ann., 659 (1962) 168, Synthesis (1974) 549).

A serious deficiency is the instability of the peptide azides which, even at slightly elevated temperature, may rearrange into the isocyanates by a Curtius degradation, and consequently form ureas and other by-products (Helv. Chim. Acta, 44 (1961) 1991, especially page 1997, Synthesis (1974) 549).

This side reaction with formation of the isocyanate and further reaction to the urea has also been observed on working up (see Examples 4.1 and 4.2). The by-product (urea derivative) is very difficult to separate from the corresponding peptide, and can be detected only by means of HPLC. The extent of this side reaction may be up to 15% (see Example 4.2).

The yields of the azide syntheses are rarely higher than 70-80% of theory. This is caused by the side reactions which have been mentioned.

The azide process cannot be utilized with a view to production scale. The hydrazoic acid or its salts which are produced during the process represent, when they exceed a certain amount, a safety risk which is difficult to overcome industrially. Thus, for example, in the course of working up a reaction involving about 25 kg of tripeptide azide, for example in an acid extraction, at least 1 kg of hydrazoic acid is produced, and this can lead to violent explosions (Lit.: Römpps Chemie Lexikon, 7th Edition, Frankh'sche Verlagshandlung, Stuttgart 1975, page 3348).

It would be necessary to develop and install a large number of costly techniques of measurement for inprocess checks in order to control this risk. In addition, it would be necessary to remove hydrazoic acid and its salts from mother liquors and aqueous extraction solutions before disposing of them, which would likewise require major analytical elaboration.

Moreover, hydrazoic acid is to be regarded as objectionable from the viewpoint of industrial hygiene; this is evident from its very low MAC value. The MAC value for HN$_3$ is 0.1 ml/m$^3$ or 0.27 mg/m$^3$ (Industrial Hazardous Materials Regulations 900, 1982).

The reasons which have been mentioned prohibit enlargement of the azide process beyond the laboratory scale.

It has now been found that, starting from the protected tripeptide of the formula II which has been prepared by low-racemization routes, in practice racemate-free products of the formula I are surprisingly obtained by means of the five coupling processes mentioned below.

The process according to the invention, for example using the PPA method, is, in contrast to the azide process, not subject to restrictions of industrial safety. Moreover, the process has likewise proved to be without problems from the standpoint of practical chemistry. The transition to production scale led to a loss neither of yield nor of purity of the products compared with the laboratory scale (Example 6.1).

The reaction of the tripeptide of the formula II with the appropriate peptide of the formula III having a free amino group and protected carboxyl group is preferably carried out in a solvent customary in peptide chemistry or in water/solvent mixtures, in the presence of a suitable condensing agent such as, for example:

1. Dicyclohexylcarbodiimide with the addition of 1-hydroxybenzotriazole (DCII/HOBt method; Lit.: Chem. Ber. 103 (1970) 788)
2. Dicyclohexylcarbodiimide with the addition of 3-hydroxy-4-oxo-3,4-dihydro-1,2,3-benzotriazine (DCCI/HOOBt method; Lit.: Chem. Ber. 103 (1970) 2034)
3. Dicyclohexylcarbodiimide with the addition of N-hydroxysuccinimide (DCCI/HONSu method; Lit.: Z. Naturforsch. 21b (1966) 426)

Alkanephosphonic anhydride, such as n-propylphosphonic anhydride (PPA method; Lit.: Angew. Chemie, Int. Ed. 19 (1980) 133)

5. Dialkylphosphinic anhydride, such as methylethylphosphonic anhydride (MEPA method; Lit.: U.S. Pat. No. 4,426,325).

When, in the gonadorelin analog which is to be synthesized, the amino acid in position 6 is to be an acid-labile amino acid derivative (such as, for example, D-Ser (Bu$^t$), D-Glu(OBu$^t$), L-Lys(Boc) etc.), the intermediate of the formula I with X=OBu$^t$ is of no use; the synthetic route must then pass via intermediates of the formula I with X≠OBu$^t$.

The solvents which are suitable for use in the process according to the invention are, for reasons of solubility, usually polar solvents such as, for example, dimethylacetamide, dimethylformamide, dimethyl sulfoxide, phosphoric tris(dimethylamide), N-methylpyrrolidone, water, or mixtures of the solvents mentioned with water. The latter applies in particular to the MEPA process. However, chloroform, methylene chloride or ethyl acetate are also used. The synthesis can be carried out between −10° C. and room temperature. It is preferable to start at about 0° C. and later to increase to room temperature.

A preferred variant of the process is one wherein A$^1$ denotes Trp, A$^2$ denotes Ser, A$^3$ denotes Tyr, A$^4$ denotes Gly, D-Ala, D-Leu, D-Ser (Bu$^t$), D-Trp, D-Phe, D-Gln (cyclohexyl), D-naphthylalanine, D-benzylhistidine, D-Thr(Bu$^t$), D-Cys(Bu$^t$), D-Asp(OBu$^t$), D-Glu(OBu$^t$), D-Orn(Boc) or D-Lys(Boc), A$^5$ denotes Leu, and X denotes OBu$^t$, Arg-Pro-NHC$_2$H$_5$, Arg-Pro-Gly-NH$_2$ or Arg-Pro-NH-NH-CO-NH$_2$.

Processes for the preparation of U-Trp-Ser-Tyr-Gly-Leu-Arg-Pro-Gly-NH$_2$ and U-Trp-Ser-Tyr-D-Ser(-Bu$^t$)-Leu-Arg-Pro-NHC$_2$H$_5$, in which U is defined as above, are particularly preferred.

Those urethane protective groups U (see Kontakte Merck 3/79, pages 14 and 16) which can be eliminated by hydrogenolysis are preferred, such as Z, Z(NO$_2$), Pyoc, Z(Hal$_n$), Dobz or Moc, but in particular Z.

The surprisingly low degree of racemization when the process according to the invention is used has been demonstrated by means of high-pressure liquid chromatography (HPLC) on the unprotected peptides of the formula I (U=hydrogen). When such a heptapeptide or octapeptide of the formula I, in which D-Tyr had been incorporated in place of Tyr in position A$^3$, was prepared as described above, the product obtained was necessarily that which would occur in the case where racemization of the compound with A$^3$=Tyr had taken place during coupling. Since these two diastereomers can be separated as the unprotected peptides by HPLC, it was thus possible to determine the extent of racemization in the individual coupling methods.

TAB. I DEGREE OF RACEMIZATION—EXAMPLE

Z-Trp-Ser-Tyr-D-Ser(Bu$^t$)-Leu-Arg-Pro-NHEt; the synthesis of the compounds mentioned is carried out by the various methods, and in each case the reaction product is, without intermediate purification, subjected to hydrogenation and characterized as H-Trp-Ser-Tly-D-Ser(Bu$^t$)-Leu-Arg-Pro-NHEtby HPLC.

HPLC method:

Column: Necluosil ® 5SA (4×300 mm); eluting agent: 40% buffer/60% acetonitrile (buffer: 1% strength KH$_2$PO$_4$; pH: 5.8), flow rate: 1 ml/min; detector: UV-220 nm.

| Synthetic method | % age of the D-isomer$^{(+)}$ |
|---|---|
| DCCI/HOBt | 3–5 |
| DCCI/HOOBt | 1.5–2.5 |
| DCCI/HONSu | 1.5–2.5 |
| PPA | 1–2 |
| MEPA | 1.5–2.5 |
| Azide | 1–2 |

$^{(+)}$The retention time of the D-isomer H—Trp—Ser—D-Tyr—D-Ser(Bu$^t$)—Leu—Arg—Pro—NHEt was determined after specific preparation of the compound by the PPA method.

It is noteworthy that, in addition to the small extent of racemization when the PPA method is used, the yield and the purity of the products are particularly high

TAB. II COMPARISON: PURITY/YIELD

Example: Z-Trp-Ser-Tyr-D-Ser(Bu$^t$)-Leu-Arg-Pro-NHEt; the reaction product is weighed after isolation, and from this the theoretical yield is calculated, and a relative purity index is derived using HPLC. HPLC method: column: Nucleosil ® 5SA (4×300 mm); eluting agent: 40% buffer/60% acetonitrile (buffer: 1% strength KH$_2$PO$_4$; pH: 5.8); flow rate: 1 ml/min. Detector: UV-220 nm.

| Synthetic method | Yield (% age of theory) | Purity; % age area$^{(+)}$ |
|---|---|---|
| DCCI/HOBt | 69 | 73 |
| DCCI/HOOBt | 72 | 75 |
| DCCI/HONSu | 75 | 77 |
| PPA | 85–90 | 80 |
| Synthetic method | Yield (% age of theory) | Purity; % age area$^{(+)}$ |
| MEPA | 63 | 76 |
| Azide | 70–80 | 55 |

$^{(+)}$Relative purity index by HPLC; the total of the peak areas for all UV-absorbing substances (at 220 nm) in the chromatogram of the reaction product is set equal to 100. The desired substance accounts for x% area (100% method).

The invention also relates to tripeptides of the formula II $$U—A^1—A^2—A^3—OH \qquad (II)$$

in which U, A$^1$, A$^2$ and A$^3$ are as defined above, in particular

Z—Trp—Ser—Tyr—OH, and to a process for the preparation of these tripeptides by fragment condensation, as is customary in peptide chemistry, of peptide fragments in accordance with condensation schemes (1−2)+3 or 1+(2−3), where appropriate intermediate blocking of other functional groups being carried out with, where appropriate, protective groups which can be eliminated in alkaline or acid medium.

The synthesis of the tripeptides of the formula II is preferably carried out by low-racemization routes, i.e. avoiding synthetic stages which include a hydrolysis reaction, such as, for example, the synthesis of Z-Trp-Ser-Tyr-OH which is described in the scheme below.

Scheme:

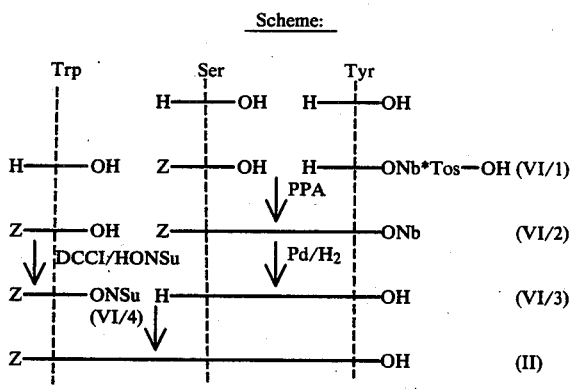

The compounds II, VI/2 and VI/3 are not described in the literature. Compound VI/1 was prepared by the method of Shields, McGregor and Carpenter, J. Org. Chem., 26 (1961) 1491, and compound VI/4 was prepared by the method of E. Wünsch and K. H. Deimer, Hoppe-Seyler's Z. Physiol. Chem., 353 (1972) 1246.

It emerged that the preparation route (via VI/1 VI/4) led to the objective unusually rapidly and straightforwardly, since the individual intermediates were produced as crystals, in good yield and high purity. The hydrogenation step in which the protective groups are removed from the dipeptide is remarkably straightforward to carry out (Example 5.2).

The abbreviations used have the following meanings:

| | |
|---|---|
| Boc | tert.-butyloxycarbonyl |
| DCCI | dicyclohexylcarbodiimide |
| DMF | dimethylformamide |
| Et | ethyl |
| HOBt | 1-hydroxybenzotriazole |
| HONSu | N—hydroxysuccinimide |
| HOOBt | 3-hydroxy-4-oxo-3,4-dihydro-1,2,3-benzotriazine |
| MEPA | methylethylphosphinic anhydride |
| ONb | p-nitrobenzyl ester |
| ONSu | N—hydroxysuccinimide ester |
| OBu$^t$ | tert.-butyl ester |
| PPA | n-propylphosphonic anhydride |
| Bu$^t$ | tert.-butyl ether |
| Tos-OH | p-toluenesulfonic acid |
| Z | benzyloxycarbonyl |

The examples which follow are intended to illustrate the process according to the invention without restricting the invention to the peptides which are mentioned here as representatives. Some of the examples describe experiments for comparison with processes of the state of the art.

EXAMPLE 1.1

Preparation of
Z-Trp-Ser-Tyr-D-Ser(Bu$^t$)-Leu-Arg-Pro-NHEt*Tos-OH using DCCI/HOBt 29.4 g (0.05 mole) of Z-Trp-Ser-Tyr-OH, 44.7 g (0.05 mole) of H-D-Ser(Bu$^t$)-Leu-Arg-Pro-NHEt*Tos-OH and 6.75 g of 1-hydroxybenzotriazole are dissolved in 250 ml of DMF, and the solution is cooled to +5° C. 6.4 ml of N-ethylmorpholine and 11.3 g of DCCI are added to the solution and, when addition is complete, the temperature is raised to about 20° C. After stirring overnight, the precipitated dicyclohexylurea is filtered off with suction, and the filtrate is evaporated to a residue. This is taken up in 600 ml of butanol and extracted with 2×150 ml of sodium carbonate solution (5% strength), 150 ml of sodium chloride solution (13% strength), 150 ml of KHSO$_4$ solution (10% strength) and 150 ml of sodium chloride solution (5% strength). The organic phase is concentrated, the precipitated sodium chloride is filtered off, and the concentrated solution (200 ml) is stirred into 1.5 l of diisopropyl ether. After filtration and washing with 200 ml of diisopropyl ether, the substance is dried over P$_2$O$_5$ in vacuo.

Yield: 44.8 g (69% of theory). $[\alpha]_D^{22}$: −31.6° (c=1, dimethylacetamide).

EXAMPLE 1.2

Preparation of
Z-Trp-Ser-Tyr-D-Ser(Bu$^t$)-Leu-Arg-Pro-NHET*Tos-OH using DCCI/HOOBt The process is carried out as in Example 1.1, but 8.15 g of 3-hydroxy-4-oxo-3,4-dihydroxy-1,2,3-benzotriazine (HOOBt) are used in place of 1-hydroxybenzotriazole.

Yield: 46.7 g (72% of theory).
$[\alpha]_D^{22}$: −31° (c=1, dimethylacetamide).

EXAMPLE 1.3

Preparation of
Z-Trp-Ser-Tyr-D-Ser(Bu$^t$)-Leu-Arg-Pro-NHEt*Tos-OH using DCCI/HONSu The process is carried out as in Example 1.1, but 5.75 g of N-hydroxysuccinimide (HONSu) are used in place of 1-hydroxybenzotriazole:

Yield: 48.7 g (75% of theory).
$[\alpha]_D^{22}$: −32° (c=1, dimethylacetamide).

EXAMPLE 1.4

Preparation of
Z-Trp-Ser-Tyr-D-Ser(Bu$^t$)-Leu-Arg-Pro-NHEt*Tos-OH using PPA 6.8 g (11.5 mmol) of Z-Trp-Ser-Tyr-OH and 10.3 g (11.5 mmol) of H-D-Ser(Bu$^t$)-Leu-Arg-Pro-NHEt*Tos-OH are dissolved in 65 ml of DMF at room temperature, and the solution is cooled to +5° C. Then, within 20 min., 11.1 ml of N-ethylmorpholine and 11.1 ml of n-propylphosphonic anhydride (50% by weight in methylene chloride) are simultaneously added dropwise from two dropping funnels. The reaction solution is stirred overnight (at room temperature), concentrated to about 20 ml in vacuo, and the residue is taken up in 150 ml of n-butanol. The butanol solution is extracted 2× with 30 ml each time of sodium carbonate solution (5% strength) 30 ml of sodium chloride solution (13% strength), 150 ml of KHSO$_4$ solution (10% strength) and 150 ml of sodium chloride solution (5% strength), concentrated in vacuo, the precipitated sodium chloride is filtered off, and the concentrated solution is added dropwise to about 250 ml of diisopropyl ether. After filtration and washing with 30–40 ml of diisopropyl ether, the substance is dried over $P_2O_5$ in vacuo.

Yield: 13.1 g (88% of theory).
$[\alpha]_D^{22}$: −33.7°(c=1, dimethylacetamide).

EXAMPLE 1.5

Preparation of Z-Trp-Ser-Tyr-D-Ser(Bu$^t$)-Leu-Arg-Pro-NHEt*Tos-OH using MEPA

The process is essentially carried out as in Example 1.4, apart from the following differences:

The peptides which are to be coupled are dissolved in 30 ml each of DMF and water; 2.3 g of MEPA are diluted with 5 ml of DMF and added dropwise; the pH is adjusted to pH 7.5 with about 3 ml of N-ethylmorpholine.

Yield: 9.4 g (63% of theory).
$[\alpha]_D^{22}$: −30.4° (c=1, dimethylacetamide).

EXAMPLE 1.6

Preparation of Z-Trp-Ser-Tyr-D-Ser(Bu$^t$)-Leu-Arg-Pro-NHEt*HCl by the azide process 50 g (83 mmol) of Z-Trp-Ser-Tyr-N$_2$H$_3$ are dissolved in 350 ml of DMF, the solution is cooled to −30° C., 45 ml of 8N HCl in dioxane are allowed to run in over the coarse of 20 min, 12.5 ml of t-butyl nitrate (dissolved in 100 ml of dioxane) are metered in within 20 min at at least −20° C., then the mixture is stirred at −20° C. for 20 min, cooled to −30° C., and 45.7 ml of N-ethyl-morpholine are added. 55 g (61 mmol) of H-D-Ser(Bu$^t$)-Leu-Arg-Pro-NHEt*2 Tos-Oh, which is dissolved in 150 ml of DMF to which are added 15.2 ml of N-ethylmorpholine, are added to the azide solution thus prepared. The reaction temperature is raised to +5° C., and stirring of the mixture is continued for 20 hours.

Then the reaction solution is partitioned between 400 ml of n-butanol and 4 l of a 25% strength sodium chloride solution. The aqueous phase is extracted three times more with 200 ml of n-butanol each time, and the combined organic phases are extracted three times with 200 ml of a 6.7% strength KHSO$_4$/3.3% strength K$_2$SO$_4$ solution each time. Following extraction with 200 ml of 25% strength sodium chloride solution, extraction is carried out with 200 ml of a 5% strength bicarbonate solution. The butanol phase is evaporated in vacuo, and the still liquid concentrate is introduced into 1 l of ethyl acetate, stirring vigorously. The precipitate which has separated out is filtered off, washed with 200 ml of ethyl acetate, and dried in vacuo.

Yield: 51.7 g (73% of theory).
$[\alpha]_D^{22}$: −31.8° (c=1 in methanol).

EXAMPLE 2.1

Preparation of Z-Trp-Ser-Tyr-Gly-Leu-Arg-Pro-Gly-NH$_2$*Tos-OH using PPA 29.4 g (0.05 mole) of Z-Trp-Ser-Tyr-OH and 42.08 g (0.05 mole) of H-Gly-Leu-Arg-Pro-Gly-NH$_2$*2 Tos-OH are dissolved in 200 ml of DMF, the solution is cooled to about +5° C., and 48.6 ml of N-ethylmorpholine are added. Then, within 20–30 min, 47.3 ml of PPA (50% strength in methylene chloride) are added dropwise, the temperature of the reaction mixture is brought to room temperature, and it is stirred overnight. The test of conversion is carried out using a TLC check with butanol/glacial acetic acid/water (3:1:1) as the mobile phase. After concentration of the solution to about 100 ml, it is taken up in 600 ml of butanol and extracted with 2×150 ml of sodium carbonate solution (5% strength), 150 ml of sodium chloride solution (13% strength), 150 ml of KHSO$_4$ solution (10% strength) and 150 ml of sodium chloride solution (5% strength). The organic phase is concentrated, the precipitated sodium chloride is filtered off, and the concentrated solution (200 ml) is stirred into 1.5 l of diisopropyl ether. After filtration and washing with 200 ml of diisopropyl ether, the substance is dried over $P_2O_5$ in vacuo.

Yield: 55.2 g (89% of theory).
$[\alpha]_D^{22}$: −30.1° (c=1, methanol).

EXAMPLE 2.2

Preparation of Z-Trp-Ser-Tyr-Gly-Leu-Arg-Pro-Gly-NH*Tos-OH by the azide process 57.7 g (95.8 mmol) of Z-Trp-Ser-Tyr-N$_2$H$_3$ are dissolved in 400 ml of DMF, the solution is cooled to −30° C., 43.5 ml of 8N HCl in dioxane are allowed to run in over the course of 20 min, 13.9 ml of t-butyl nitrite (dissolved in 125 ml of dioxane) are metered in at at least −20° C. within 20 min, then the mixture is stirred at −20° C. for 20 min, cooled to −30° C. and 50 ml of n-ethylmorpholine are added. Now 70 g (83 mmol) of H-Gly-Leu-Arg-Pro-Gly-NH$_2$*2 Tos-OH, which are dissolved in 400 ml of DMF and to which 30 ml of N-ethylmorpholine have been added, are added to the azide solution. The reaction temperature is raised to +5° C., and stirring of the mixture is continued for 20 hours.

Then the reaction solution is partitioned between 400 ml of n-butanol and 5 l of a 25% strength sodium chloride solution. The aqueous phase is extracted twice more with 200 ml of n-butanol each time, and the combined organic phases are extracted twice with 250 ml of an 8% strength bicarbonate solution each time and four times with 150 ml of a 13% strength sodium chloride solution each time. The butanol phase is dried over sodium sulfate and filtered. The butanol solution is then stirred into 6 l of ethyl acetate, and the precipitate which has separated out is filtered, washed with 500 ml of ethyl acetate and dried in vacuo.

Yield: 73 g (71% of theory).
$[\alpha]_d^{22}$: −31.8° (c=1, methanol).

EXAMPLE 3

Preparation of Z-Trp-Ser-Tyr-gly-Leu-OBu$^t$ using PPA 58.9 g (0.1 mole) of Z-Trp-Ser-Tyr-OH and 41.7 g (0.1 mole) of H-Gly-Leu-OBu$^t$* Tos-OH are dissolved in 400 ml of CH$_2$Cl$_2$, and the solution is cooled to 0° . . . +5° C. 96.5 ml of N-ethylmorpholine and 96.5 ml of n-propylphosphonic anhydride solution (50% by weight in methylene chloride) are added simultaneously from two dropping funnels, while cooling, over the course of 20–30 min. The reaction solution is then warmed to room temperature and, after 3–20 hours, is extracted with 2×150 ml of sodium carbonate solution (5% strength), 150 ml of sodium chloride solution (13% strength), 150 ml of KHSO$_4$ solution (10% strength) and the sodium chloride solution (5% strength). The methylene chloride phase is evaporated in vacuo, and the residue which remains is crystallized from ethyl acetate/ligroin. After filtration and washing with 100 ml of ligroin, the substance is dried in vacuo.

Yield: 70 g (86% of theory).

$[\alpha]_D^{22}$: −25.8° (c=1, methanol).

EXAMPLE 4.1

Preparation of Z-Trp-Ser-Tyr-N$_3$ 6 g (10 mmol) of Z-Trp-Ser-Tyr-N$_2$H$_3$ are dissolved in 40 ml of DMF, the solution is cooled to −30° C., 52.5 ml (42 mmol) of 8N HCl/dioxane are allowed to run in over the course of 20 min, 1.4 ml of t-butyl nitrite (dissolved in 12 ml of dioxane) are metered in at −20° C. within 20 min, and the mixture is stirred at −20° C. for 20 min, cooled to −30° C., and 5.3 ml of N-ethylmorpholine are added. The cold solution is introduced into 650 ml of cold diether ether, the supernatant is removed by decantation from the precipitate which is again stirred with cold ether and the latter is decanted off. The residue is taken up in 40 ml of methylene chloride, extracted three times with about 25 g of ice-water, and the solution is dried over sodium sulfate. The solution thus obtained is stored in a refrigerator until the IR spectra are recorded. In the IR, the fresh solution shows a sharp band at 4.7 μm, while after about 1 h a new signal appears at 4.5 μm, and this is larger than the signal at 4.7 μm after 24 hours. According to Schwyzer et al., Helv. chim. Acta, 44 (1961) 1991, this observation is to be interpreted as a Curtius rearrangement of an acid azide in the corresponding isocyanate.

EXAMPLE 4.2

Reaction of an old azide solution with H-D-Ser(Bu$^t$)-Leu-Arg-Pro-NHE*2 Tos-OH

A solution prepared in accordance with Example 4.1 is stored at refrigerator temperature for one day, and a solution of 5 g (5.6 mmol) of H-D-Ser(Bu$^t$)-Leu-Arg-Pro-NHEt*2 Tos-OH in 15 ml of DMF together with 1 ml of N-ethylmorpholine is added, and the mixture is again stored at +5° C. overnight. The product is isolated by the work-up process in Example 1.6 and subjected to hydrogenation in a methanolic solution in the presence of palladium on active charcoal. The reaction product obtained after hydrogenation was investigated by HPLC (system: column: Nucleosil ® 5SA (4×300 mm); eluting agent: 40% buffer/60% acetonitrile (buffer: 1% strength KH$_2$PO$_4$; pH: 5.8) flow rate: 1 ml/min; detector: UV-220 nm). In this, in addition to the main product H-Trp-Ser-Tyr-D-Ser(Bu$^t$)-Leu-Arg-Pro-NHEt with a retention time of about 25 min, another intense, by-product peak with a retention time of about 30 min appeared. A comparative investigation of the corresponding products which had been prepared in accordance with Examples 1.1-1.6 showed that only the product from 1.6 contained the by-product peak with a retention time of about 30 min, with about 15% area, while the products from the new process according to the invention did not show this additional component.

Apparently, the by-product with the retention time of about 30 min in the HPLC is a urea derivative which can be regarded as a product secondary to the Curtius rearrangement of the azide into the isocyanate which was observed in Example 4.1.

EXAMPLE 5.1

Preparation of Z-Ser-Tyr-ONb 244.0 g of the p-nitrobenzyl ester of tyrosine toluenesulfonate and 119.6 g of benzyloxycarbonylserine are dissolved in 1.8 l of dimethylformamide at room temperature in a 4 l four-necked flask, and the solution is cooled to 0°−+5° C. At about 5° C., 300.0 ml of N-etlmorpholine and, over the course of 20 min, 275.0 ml of a solution of propanephosphonic anhydride in methylene chloride are added dropwise.

The temperature is then raised to room temperature within half an hour.

After about 4 hours, distillation of the DMF in vacuo is started (in a rotary evaporator). As soon as the distillation is complete, the residue is dissolved in ethyl acetate and stirred with water to give a clear solution. The pH of the aqueous phase should be about pH 6. The ethyl acetate phase is separated off in a separating funnel, and the aqueous phase is again extracted by stirring eith ethyl acetate, the two organic phases are combined and, after a TLC check, the remaining aqueous phase is discarded. The organic phase is extracted by stirring with KHSO$_4$ solution, with NaHCO$_3$ solution and with water and is separated off. The ethyl acetate solution is evaporated to dryness in vacuo, and the oily residue is stirred with diethyl ether, whereupon the oil completely crystallizes. The product is filtered off with suction and dried in vacuo.

Yield: 174.8 g (65% of theory).

Melting point: 202°-208° (decomposition), $[\alpha]_D^{22}$: −13.2° (c=1, dimethylacetamide).

EXAMPLE 5.2

Preparation of seryltyrosine (H-Ser-Tyr-OH) 177.0 g of the p-nitrobenzyl ester of benzyloxycarbonylseryltrosine (Z-Ser-Tyr-ONb) are dissolved in 2.0 l of methanol and 1.0 l of dimethylformamide at room temperature in a 4 l four-necked flask. 10.0 g of catalyst (Pd/active charcoal) which is moist with water are added to the solution, and hydrogenation is carried out at room temperature for 2 hours, with stirring.

The mixture is then filtered washing twice with methanol/DMF (2:1). The filtrate is evaporated to dryness in vacuo. The residue is stirred into diisopropyl ether, the product resulting as a flocculent, rapidly sedimenting precipitate which can be filtered off with suction. The product is dried in vacuo.

Yield: 100.3 g (87% of theory).

$[\alpha]_D^{22}$: +33.2° (c=1, methanol).

EXAMPLE 5.3

Preparation of Z-Trp-Ser-Tyr-OH 100.3 g of seryltyrosine (purity: 77%) are suspended in 500 ml of DMF. 249 g of a 50% strength solution of Z-Trp-ONSu in DMF and 35 ml of N-ethylmorpholine are added to the suspension. The suspension has dissolved after stirring at room temperature for about 2 hours. The solvent is removed in vacuo, and the residue is taken up in 500 ml of ethyl acetate. The ethyl acetate phase is extracted by stirring with 1 l of 85% strength sodium bicarbonate solution and, after a TLC check, the organic phase is discarded, and 1 l of ethyl acetate is again added to the aqueous solution which is cautiously acidified with 1.4 l of a 10% strength KHSO$_4$ solution.

The organic phase is separated off, washed with 1 l of water and concentrated to about 300 ml in vacuo, whereupon the product already starts to crystallize out. The crystallization is completed by addition of 1.5 l of diisopropyl ether, and the precipitate is filtered off and dried in vacuo at 40° C.

Yield: 126.7 g (75% of theory).
Melting point: 165°–172° C.;
$[\alpha]_D^{22}$: +6.2° (c=1, methanol).

EXAMPLE 6.1

Preparation of
Z-Trp-Ser-Tyr-D-Ser(Bu$^t$)-Leu-Arg-Pro-NHEt*Tos-OH 60b kg (63 l) of DMF are initially introduced into a 100 l stirred vessel, and 10.34 kg (11.5 mole) of H-D-Ser(Bu$^t$)-Leu-Arg-Pro-NHEt*Tos-OH and 6.77 kg (11.5 mole) of Z-Trp-Ser-Tyr-OH are successively dissolved in this, and the solution is cooled to +5° C. 10.13 kg (11.12 l) of N-ethylmorpholine are introduced into the feed vessel, and initially 1.5 l of this are allowed to run into the reaction solution.

Over a period of about 1 hour, at between +5° and +10° C., 15.3 kg (11.1 l) of n-propylphosphonic anhydride (50% strength in methylene chloride), together with the remaining amount of N-ethylmorpholine, are pumped in. After addition is complete, the reaction temperature is raised to about 25° C., and the batch is stirred for 5 hours. The reaction solution is then concentrated to a residual volume of about 25 l by vacuum distillation. The concentrated residue is transferred with 150 l of n-butanol into a 250 l stirred vessel with a separation vessel of equal size—then the butanol phase is extracted successively with the following aqueous solutions: (1) sodium carbonate solution, (2) sodium chloride solution, (3) sodium carbonate solution, (4) water, (5) KHSO$_4$ solution and (5) sodium chloride solution.

The organic phase is concentrated to about 50 l, the concentrate is transferred to the feed vessel of the stirred vessel, the stirred vessel is charged with 165 kg (230 l) of diisopropyl ether, and 25 l of the butanol concentrate are metered into this stirred liquid over the course of 1 hour. The resultaing precipitate is stirred for a further 1 hour and finally centrifuged down. The other half of the butanol concentrate is subjected to the same process. The product is dried in vacuo at 35°–40° C.

Yield: 13.5 kg (90% of theory).
$[\alpha]_D^{22}$: −33.7° (c=1, dimethylacetamide).

We claim:

1. A process for the preparation of peptides of the Formula I $$U-A^1-A^2-A^3-A^4-A^5-X \qquad (I)$$

wherein
U denotes a urethane protective group,
$A^1$ denotes Trp or D-Trp,
$A^2$ denotes Ser, Ala or Thr,
$A^3$ denotes Tyr or Phe,
$A^4$ denotes Gly, the residue of a D-amino acid or the residue of a D-amino acid derivative,
$A^5$ denotes Leu, N-methyl-Leu, N-ethyl-Leu, Ser(Bu$^t$), Cys(Bu$^t$), Asp(OBu$^t$), Glu(OBu$^t$), Orn(Boc) or Lys(Boc) and
X denotes OBu$^t$ or $A^6$—Pro—Y,
where
$A^6$ represents Arg, Orn, Lys or homoarginine, and
Y represents Gly—NH$_2$, NH—NH—CO—NH$_2$, (C$_1$–C$_3$)-alkylamino, cyclopropylamino, (C$_1$–C$_3$)-alkylamino which is substituted with hydroxyl or fluorine, or cycloalkylamino which is substituted with hydroxyl or fluorine, which process comprises reacting a tripeptide of the formula II $$U-A^1-A^2-A^3-OH \qquad (II)$$

having a free carboxyl group, in which U, $A^1$, $A^2$ and $A^3$ have the above-mentioned meaning, with a peptide of the formula III $$H-A^4-A^5-X \qquad (III)$$

having a free amino group and a protected carboxyl group, in which $A^4$, $A^5$ and X have the above-mentioned meaning, or its derivative having a free amino group and a protected carboxyl group in the presence of a condensing agent.

2. The process as claimed in claim 1, wherein U denotes benzyloxycarbonyl (Z).

3. The process as claimed in claim 1, wherein $A^1$ denotes Trp, $A^2$ denotes Ser, $A^3$ denotes Tyr, $A^4$ denotes Gly, D-Ala, D-Leu, D-Ser(Bu$^t$), D-Trp, D-Phe, D-Gln(cyclohexyl), D-naphthylalanine, benzylhistidine, D-Thr(Bu$^t$), D-Cys(Bu$^t$), D-Asp(OBu$^t$), D-Glu(OBu$^t$), D-Orn(Boc) or D-Lys (Boc), $A^5$ denotes Lue, and X denotes OBu$^t$, Arg-Pro-NHC$_2$H$_5$, Arg-Pro-Gly-NH$_2$ or Arg-Pro-NH-NH-CO-NH$_2$.

4. The process as claimed in claim 1 for the preparation of

U-Trp-Ser-Tyr-Gly-Leu-Arg-Pro-Gly-NH$_2$.

5. The process as claimed in claim 1 for the preparation of

U-Trp-Ser-Tyr-D-Ser(Bu$^t$)-Leu-Arg-Pro-NHC$_2$H$_5$.

6. The process as claimed in claim 1, which is carried out in the presence of dicyclohexylcarbodiimide with the addition of 1-hydroxybenzotriazole or 3-hydroxy-4-oxo-3,4-dihydroxy-1,2,3-benzotriazine or N-hydroxysuccinimide.

7. The process as claimed in claim 1, which is carried out in the presence of anhydrides of alkanephosphonic acid or of dialkylaphosphonic acids.

8. The process as claimed in claim 7, which is carried out in the presence of n-propylphosphonic anhydride or methylethylphosphinic anhydride.

9. A tripeptide of the formula II $$U-A^1-A^2-A^3-OH \qquad (II)$$

in which U, $A^1$, $A^2$ and $A^3$ are defined as in claim 1.

10. Z—Trp—Ser—Tyr—OH.

* * * * *

UNITED STATES PATENT AND TRADEMARK OFFICE
CERTIFICATE OF CORRECTION

PATENT NO. : 4,691,008
DATED : September 1, 1987
INVENTOR(S) : Rainer Uhmann et al It is certified that error appears in the above-identified patent and that said Letters Patent is hereby corrected as shown below:

In claim 3, column 12, Line 36, change:

"Lue" to --Leu--.

In claim 7, column 12, Line 54, change:

"acid" to --acids--.

Signed and Sealed this

Fifth Day of April, 1988

Attest:

DONALD J. QUIGG

Attesting Officer

Commissioner of Patents and Trademarks

UNITED STATES PATENT AND TRADEMARK OFFICE
CERTIFICATE OF CORRECTION

PATENT NO. : 4,691,008
DATED : September 1, 1987
INVENTOR(S) : Rainer UHMANN, et al It is certified that error appears in the above-identified patent and that said Letters Patent is hereby corrected as shown below:

Title page:

In the priority information; change

German Application Number "341124" to --3411224--

Signed and Sealed this

Seventeenth Day of May, 1988

Attest:

DONALD J. QUIGG

*Attesting Officer*            *Commissioner of Patents and Trademarks*